United States Patent [19]

Tydeman, deceased et al.

[11] Plant 4,059

[45] June 14, 1977

[54] CHERRY ROOTSTOCK—COLT VARIETY

[75] Inventors: Henry M. Tydeman, deceased, late of East Malling, England; by Elizabeth Mary Tydeman, executrix, East Malling, England; by William Marcus Tydeman, executor, Bangor, Wales

[73] Assignee: National Seed Development Organisation Limited, Newton, England

[21] Appl. No.: 678,036

[22] Filed: Apr. 19, 1976

[51] Int. Cl.[2] ..... A01H 5/03

[52] U.S. Cl. ..... Plt./37

[58] Field of Search ..... Plt./37

*Primary Examiner*—Robert E. Bagwill
*Assistant Examiner*—James R. Feyrer
*Attorney, Agent, or Firm*—Burns, Doane, Swecker & Mathis

[57] ABSTRACT

This invention relates to a new and distinct variety of cherry tree useful as a dwarfing cherry rootstock. The new variety originated as a seedling by crossing pollen from *Prunus pseudocerasus* Lind. onto flowers of *Prunus avium* L. F 299/2. Cherry trees on the understock of this variety are approximately 50 percent of the size of like cherry trees on F 12/1 understock. Also, this variety induces higher fruit bud production on the scion on this rootstock in the early life of the grafted cherry tree than if grafted on F 12/1 understock, thus giving heavier cherry crops earlier in the life of the grafted tree.

4 Drawing Figures

SUMMARY OF THE INVENTION

The original plant was a member of a family of seedlings, Fb 2/58, produced by pollinating flowers of *Prunus avium* L. F 299/2 with pollen from *Prunus pseudocerasus* Lind. in 1958. Selection was made in 1966/1967. Following evaluation and testing the new variety was found to be useful as a dwarf cherry rootstock. Pollination, evaluation, and testing was carried out at the East Malling Research Station, Maidstone, Kent, England.

At the present time there is great interest in and demand for a dwarfing cherry rootstock. The cherry trees of the present invention satisfy this need. For instance, it has been found that cherry trees grafted upon the understock of the present variety grow to only approximately 50 percent of the size of like cherry trees on F 12/1 understock, the present commercial cherry rootstock in Great Britain. The rootstock of the present invention has been designated the Colt variety.

Cherry trees of the Colt variety may be easily propagated by hardwood and softwood cuttings. Such asexual reproductions at the East Malling Research Station have demonstrated that its distinctive characteristics including its dwarfing character are stable and are transmitted without change through succeeding propagations.

BRIEF DESCRIPTION OF THE DRAWINGS

The accompanying drawings show typical specimens of the improved cherry rootstock, wherein.

DETAILED DESCRIPTION

Figure 1:
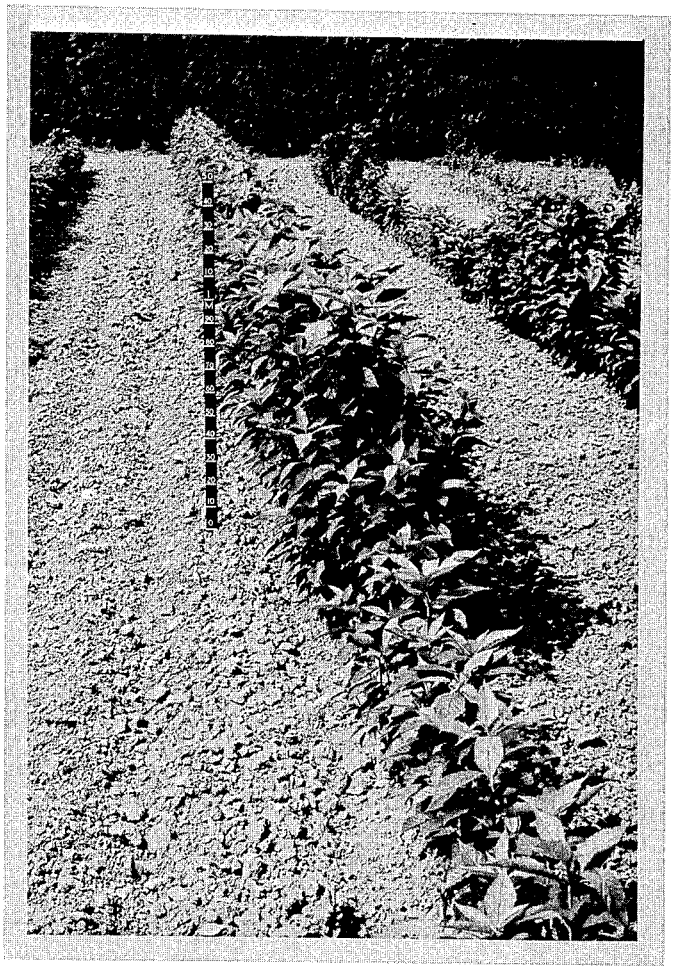
FIG. 1 is a hedge of Colt cherry rootstock planted at the East Malling Research Station in the Autumn of 1973 and photographed during August, 1975 with the height being shown in centimeters.
Figure 2:
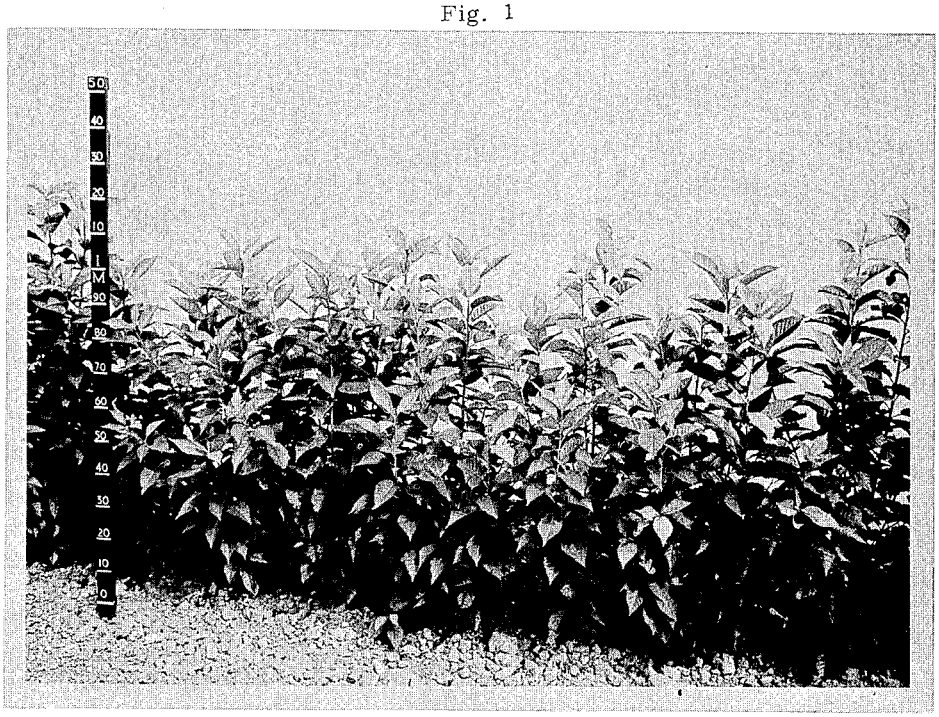
FIG. 2 is another view of the same hedge shown in FIG. 1.
Figure 3:
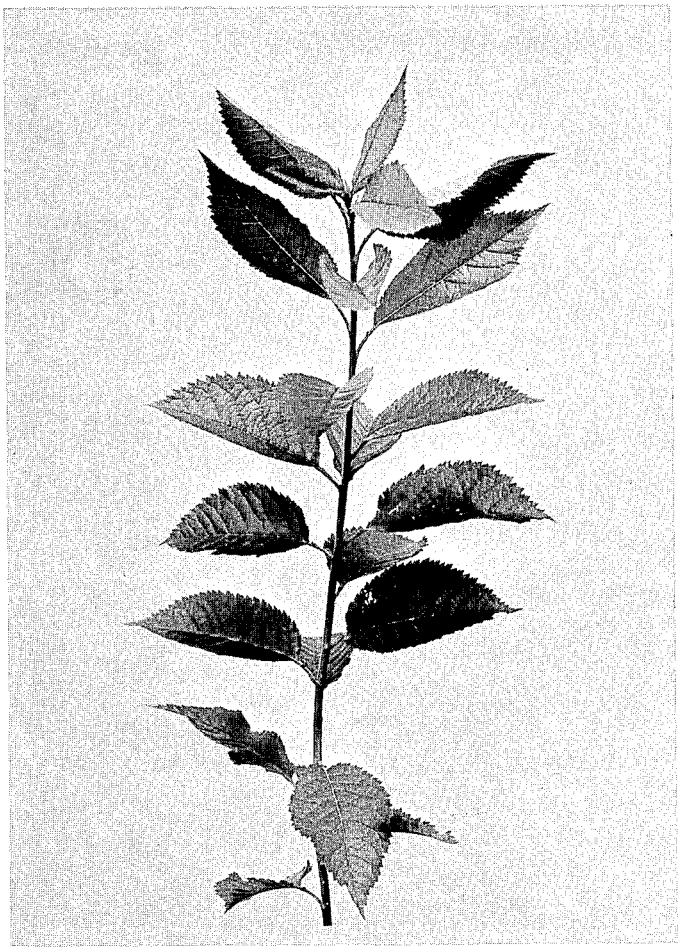
FIG. 3 is a one year old vegetative shoot of the Colt cherry rootstock grown at the East Malling Research Station.
Figure 4:
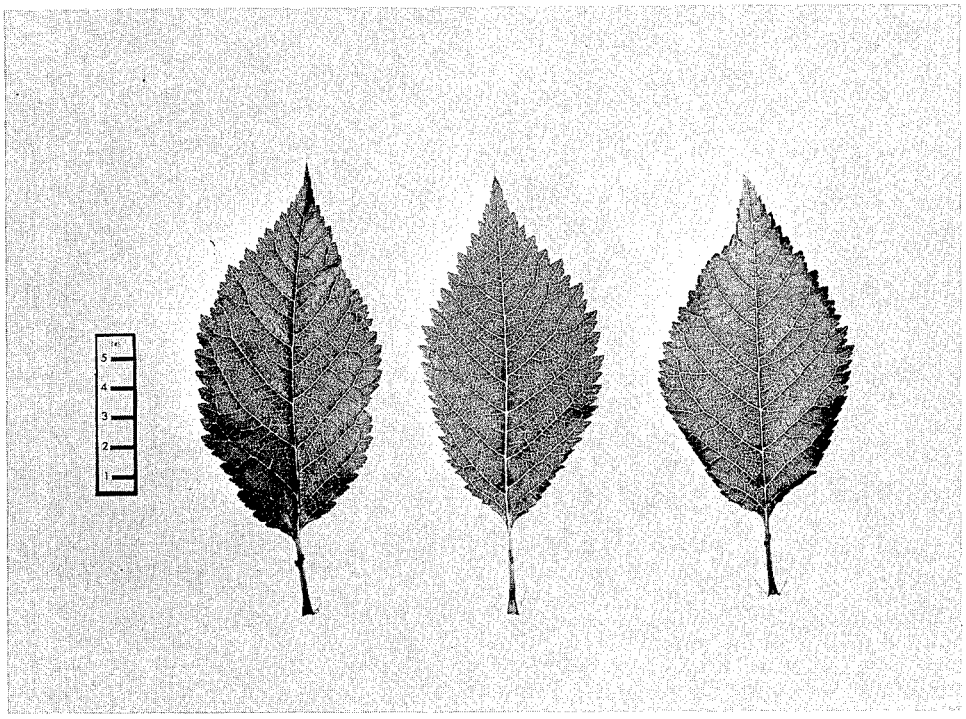
FIG. 4 illustrates leaves of the Colt cherry rootstock grown at the East Malling Research Station and photographed during October, 1975 with the dimensions being shown in centimeters.

The following is a detailed description of the new cherry rootstock's summer characteristics as observed on one year old shoots produced on hedges in the propagation nursery at the East Malling Research Station, Kent, England. These characteristics are those most often seen and used in the identification of a rootstock.

Colors of leaves and shoots vary with growing conditions and generally are not considered to be of value in identifying the rootstock. In those instances where a precise color assessment can be made reference is to Munsell Color Charts for Plant Tissues, 1st Edition (1952), Munsell Color Co., Inc., Baltimore, Md., U.S.A. In other instances general color terms are used in accordance with their ordinary dictionary significance.

Asexual reproduction of the new Colt variety by hardwood and softwood cuttings, as performed at the East Malling Research Station, shows that the described characteristics and distinctions come true to form and are transmitted through succeeding propagations.

Distinctive points

Vigorous, sturdy, erect shoots with large, bright green, slightly upturned leaves; slightly upturned petioles with conspicuous branched feathery stipules on younger leaf petioles. Growing shoots are paler green with pink color at tips.

Stems are greenish, with silver-white waxy covering in places; lenticels few, roundish to irregular in shape, whitish to brown in color.

Hedges established for 2 years or more show adventitious roots in clusters at the base of shoots of all ages by the end of the growing season.

General habit:
*Strength of growth.*—Vigorous, sturdy shoots.
*Habit of growth.*—Erect.
*Number of laterals on previous growth.*—Not observed on one year old shoots.
*Feathering on current growth.*—Usually unfeathered.
*Number of shoots on hedge.*—Moderate.

Wood: Summer.
*Color.*—Green, with silver-white waxy covering in places (Munsell 2.5GY 6/4).
*Hairiness.*—Smooth, no hairs.
*Texture.*—Ridged, especially below leaf attachment of younger leaves.

Lenticels:
*Number.*—Not very many.
*Conspicuousness.*—Summer conspicuous.
*Shape.*—Round when immature, later irregular.
*Color.*—Whitish, turning to orange-brown (Munsell 7.5YR 8/2).
*Distribution.*—Scattered.
*Size.*—Medium.

Leaves:
*Size.*—Large, length 131.23 mm; breadth 72.67 mm.
*Shape.*—Elliptic.
*Base.*—Obtuse, attenuated.
*Apex.*—Acuminate, sometimes twisted.
*Serrations.*—Dentate-serrate.
*Surface.*—Flat, veins sunken, few hairs along veins.
*Margin.*—Raised slightly.
*Pose in relation to stem.*—Slightly upturned.
*Color.*—Bright clear green.
*Hairiness on under surface.*—Few hairs on veins.
*Texture.*—Smooth upper surface, rougher lower surface.
*Color of tips of shoots.*—Pale, slightly pink when still actively growing.

Petiole:
*Shape.*—Channelled.
*Length.*—Fairly long, 21.02 mm.
*Color.*—Green, tinged red when young.
*Pose.*—Slightly upturned.
*Glands.*—Usually two, sometimes one, sometimes opposite, sometimes not.

Stipules (not always present):
*Size.*—Long, branched.
*Margin.*—Parted.
*Shape.*—Feathery.
*Pose.*—Erect.

Buds:
*Size.*—Small.
*Shape.*—Conical, spread at base.
*Compactness.*—Bud scales overlap neatly, extreme edges may be slightly ragged.
*Color.*—Warm brown.
*Hairiness.*—Very few fine hairs, sometimes a waxy coating at juncture with stem.
*Pose.*—Fairly close to shoot, almost vertical.
*Base.*—Extended.

GENERAL CHARACTERISTICS

Suckering: Few suckers are produced.

Yield potential: The Colt variety has been found to induce higher fruit bud production on the scion in the early life of the cherry tree than F 12/1, thus in favorable years giving heavier crops earlier in the tree's life. Fruit quality is equal to, or better than, that produced on F 12/1 rootstock.

Compatibility: Colt has shown itself to be compatible with all scion cherry varieties tested.

1. A new and distinct variety of cherry tree useful as a dwarfing cherry rootstock substantially as illustrated and described, produced as a seedling by crossing pollen from *Prunus pseudocerasus* Lind. onto flowers of *Prunus avium* L. F 299/2, which when used as an understock induces less growth of the cherry tree, and higher fruit bud production on the scion in the early life of the grafted cherry tree.

* * * * *